(12) United States Patent
Mou et al.

(10) Patent No.: US 11,944,412 B2
(45) Date of Patent: Apr. 2, 2024

(54) BLOOD PRESSURE DETECTION DEVICE (71) Applicant: Microjet Technology Co., Ltd., Hsinchu (TW)

(72) Inventors: Hao-Jan Mou, Hsinchu (TW); Ying-Lun Chang, Hsinchu (TW); Ching-Sung Lin, Hsinchu (TW); Chi-Feng Huang, Hsinchu (TW); Yung-Lung Han, Hsinchu (TW); Chang-Yen Tsai, Hsinchu (TW); Wei-Ming Lee, Hsinchu (TW); Chun-Yi Kuo, Hsinchu (TW); Tsung-I Lin, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 352 days.

(21) Appl. No.: 17/336,725

(22) Filed: Jun. 2, 2021

(65) Prior Publication Data
US 2021/0378530 A1 Dec. 9, 2021

(30) Foreign Application Priority Data
Jun. 5, 2020 (TW) ................................ 109118985

(51) Int. Cl.
*A61B 5/021* (2006.01)
*B81B 3/00* (2006.01)

(52) U.S. Cl.
CPC ........ *A61B 5/02133* (2013.01); *B81B 3/0021* (2013.01); *A61B 2560/0214* (2013.01);
(Continued)

(58) Field of Classification Search
None
See application file for complete search history.

(56) References Cited

U.S. PATENT DOCUMENTS 5,472,032 A * 12/1995 Winston ................ B60C 23/121
417/27
2017/0340209 A1 11/2017 Klaassen et al.
(Continued)

FOREIGN PATENT DOCUMENTS

| CN | 109505759 A | 3/2019 |
|---|---|---|
| CN | 208778196 U | 4/2019 |

(Continued)

*Primary Examiner* — Benjamin S Melhus
*Assistant Examiner* — Samuel C Kim
(74) *Attorney, Agent, or Firm* — Birch, Stewart, Kolasch & Birch, LLP (57) ABSTRACT

A blood pressure detection device manufactured by a semiconductor process includes a substrate, a microelectromechanical element, a gas-pressure-sensing element, a driving-chip element, an encapsulation layer and a valve layer. The substrate includes inlet apertures. The microelectromechanical element and the gas-pressure-sensing element are stacked and integrally formed on the substrate. The encapsulation layer is encapsulated and positioned on the substrate. A flowing-channel space is formed above the microelectromechanical element and the gas-pressure-sensing element. The encapsulation layer includes an outlet aperture in communication with an airbag. The driving-chip element controls the microelectromechanical element, the gas-pressure-sensing element and valve units to transport gas. The gas is introduced into the flowing-channel space through the inlet apertures and transported into the airbag through the outlet aperture, to inflate the airbag for blood pressure measurement, and a detection datum of blood pressure outputted by the gas-pressure-sensing element is transmitted to the microprocessor to calculate.

8 Claims, 9 Drawing Sheets

(52) U.S. Cl.
CPC ... *A61B 2562/028* (2013.01); *B81B 2201/054* (2013.01); *B81B 2203/0127* (2013.01); *B81B 2207/012* (2013.01)

(56) References Cited

U.S. PATENT DOCUMENTS

| | | | |
|---|---|---|---|
| 2019/0064104 A1* | 2/2019 | Mou | F15B 15/20 |
| 2019/0101111 A1* | 4/2019 | Mou | F04B 43/046 |
| 2019/0125965 A1* | 5/2019 | Mou | B82Y 5/00 |

FOREIGN PATENT DOCUMENTS

| | | | |
|---|---|---|---|
| CN | 109745022 A | 5/2019 | |
| CN | 110575137 A | 12/2019 | |
| CN | 210121137 U | 3/2020 | |
| TW | 201233368 A1 | 8/2012 | |
| TW | 202000129 A | 1/2020 | |
| TW | 202035275 A | 10/2020 | |

* cited by examiner

BLOOD PRESSURE DETECTION DEVICE

FIELD OF THE INVENTION

The present disclosure relates to a blood pressure detection device, and more particularly to a miniaturized blood pressure detection device manufactured by a semiconductor process.

BACKGROUND OF THE INVENTION

In recent years, owing to the awareness of personal health care, the need of regularly monitoring personal physical conditions is gradually risen. However, most of the instruments for measuring the physical conditions are stationary, and almost all people have to visit a specific medical service station or a hospital. Even through there are several measurement instruments provided for household use, the sizes of those instruments are too large and not easy to carry, and thus is difficult to satisfy the requirements of fast and convenient of the users in the modern society.

The blood pressure is regarded as the best measurement instrument to reflect the physical condition of user. As the blood vessels in people's body are like the roads all over the body, the blood pressure is like the road condition that is helpful to find out the state of blood transport. Therefore, the blood pressure can clearly reflect the condition in the body when something goes wrong.

In view of this, providing a blood pressure detection device capable of measuring the blood pressure accurately at any time, which is capable of combining with a wearable device or a portable electronic device to allow the user to quickly confirm the blood pressure status anytime, anywhere is a problem needs to resolve right now.

SUMMARY OF THE INVENTION

An object of the present disclosure is to provide a blood pressure detection device having a miniaturized structure manufactured by a semiconductor process, and capable of being combined with a wearable device or a portable electronic device, which is convenient for users to carry, and capable of achieving the blood pressure measurement without being restricted by time and place.

In accordance with an aspect of the present disclosure, a blood pressure detection device is provided. The blood pressure detection device includes a substrate, a microelectromechanical element, a gas-pressure-sensing element, a driving-chip element, an encapsulation layer and a valve layer. The substrate includes a microelectromechanical-element region, a gas-pressure-sensing region and a driving-element region. At least one inlet aperture is formed in the microelectromechanical-element region by an etching process. The microelectromechanical element manufactured by a semiconductor process is stacked and integrally formed on the microelectromechanical-element region of the substrate, and corresponds to the at least one inlet aperture to actuate transportation of gas. The gas-pressure-sensing element manufactured by a semiconductor process is stacked and integrally formed on the gas-pressure-sensing region of the substrate to detect a gas pressure and generate and output a detection datum of blood pressure. The driving-chip element manufactured by a semiconductor process is stacked and integrally formed on the driving-element region. The driving-chip element is electrically connected to the microelectromechanical element and the gas-pressure-sensing element, and includes a microprocessor. The encapsulation layer is encapsulated and positioned on the substrate. A flowing-channel space is formed above the microelectromechanical element and the gas-pressure-sensing element, an outlet aperture is formed in the encapsulation layer by an etching process, and the outlet aperture is in fluid communication with an airbag. The valve layer is formed and stacked on a bottom of the substrate by a deposition process. A valve unit is formed in the valve layer by an etching process at a position corresponding to the inlet aperture of the substrate, and the valve unit is controlled by the microprocessor of the driving-chip element to be opened or closed. The microprocessor of the driving-chip element controls driving operations of the microelectromechanical element, the gas-pressure sensing element and the valve unit, respectively. When the valve unit is opened and the microelectromechanical element is enabled to actuate the transportation of the gas, the gas is introduced into the flowing-channel space through the at least one inlet aperture of the substrate, flows through the outlet aperture of the encapsulation layer, and transported into and inflated the airbag for carrying out blood pressure measurement, and the detection datum of blood pressure outputted by the gas-pressure-sensing element is transmitted to the microprocessor to calculate and output.

BRIEF DESCRIPTION OF THE DRAWINGS

The above contents of the present disclosure will become more readily apparent to those ordinarily skilled in the art after reviewing the following detailed description and accompanying drawings, in which.

DETAILED DESCRIPTION OF THE PREFERRED EMBODIMENT

The present disclosure will now be described more specifically with reference to the following embodiments. It is to be noted that the following descriptions of preferred embodiments of this disclosure are presented herein for purpose of illustration and description only. It is not intended to be exhaustive or to be limited to the precise form disclosed.

Figure 1:
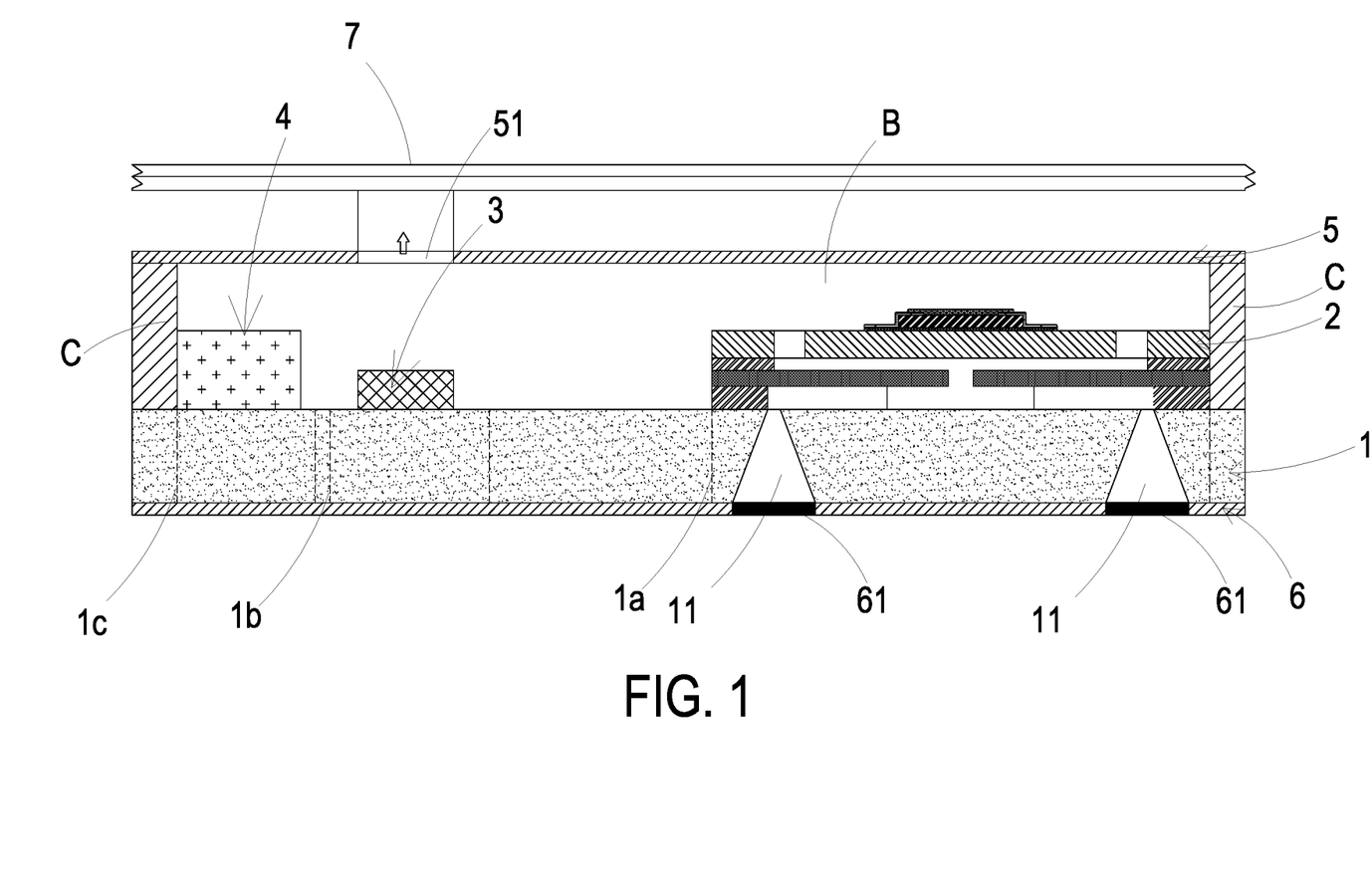
FIG. 1 shows a cross sectional view illustrating a blood pressure detection device according to an embodiment of the present disclosure.

Please refer to FIG. 1. The present disclosure provides a blood pressure detection device manufactured by a semiconductor process and includes a substrate 1, a microelectromechanical element 2, a gas-pressure-sensing element 3, a driving-chip element 4, an encapsulation layer 5 and a valve layer 6.

Preferably but not exclusively, the substrate 1 is a silicon substrate and includes a microelectromechanical-element region 1a, a gas-pressure-sensing region 1b and a driving-element region 1c. In the embodiment, at least one inlet aperture 11 is formed in the microelectromechanical-element region 1a by an etching process.

Figure 2A:
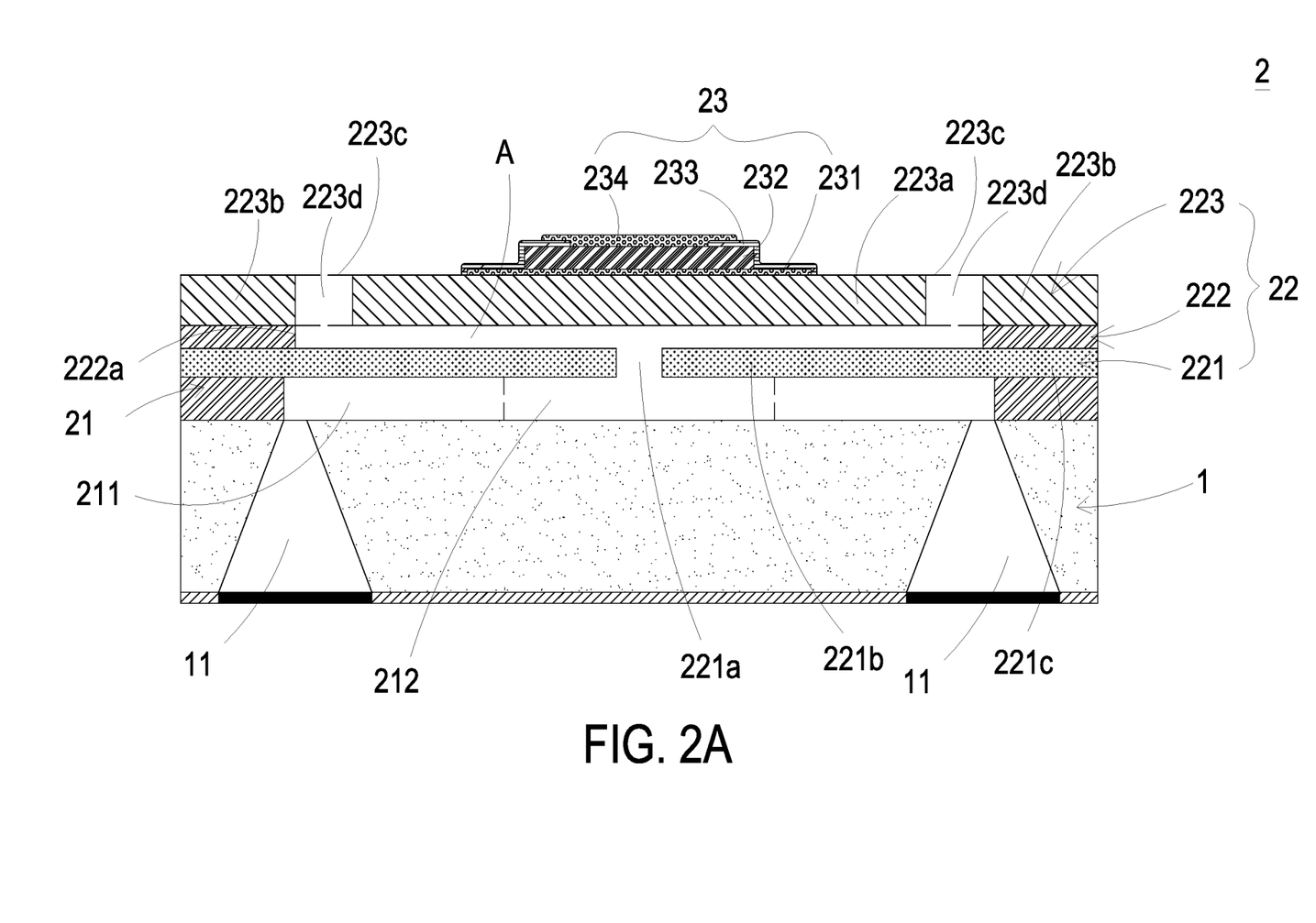
FIG. 2A shows a cross sectional view illustrating the microelectromechanical element of the blood pressure detection device according to the embodiment of the present disclosure.
Figure 2B:
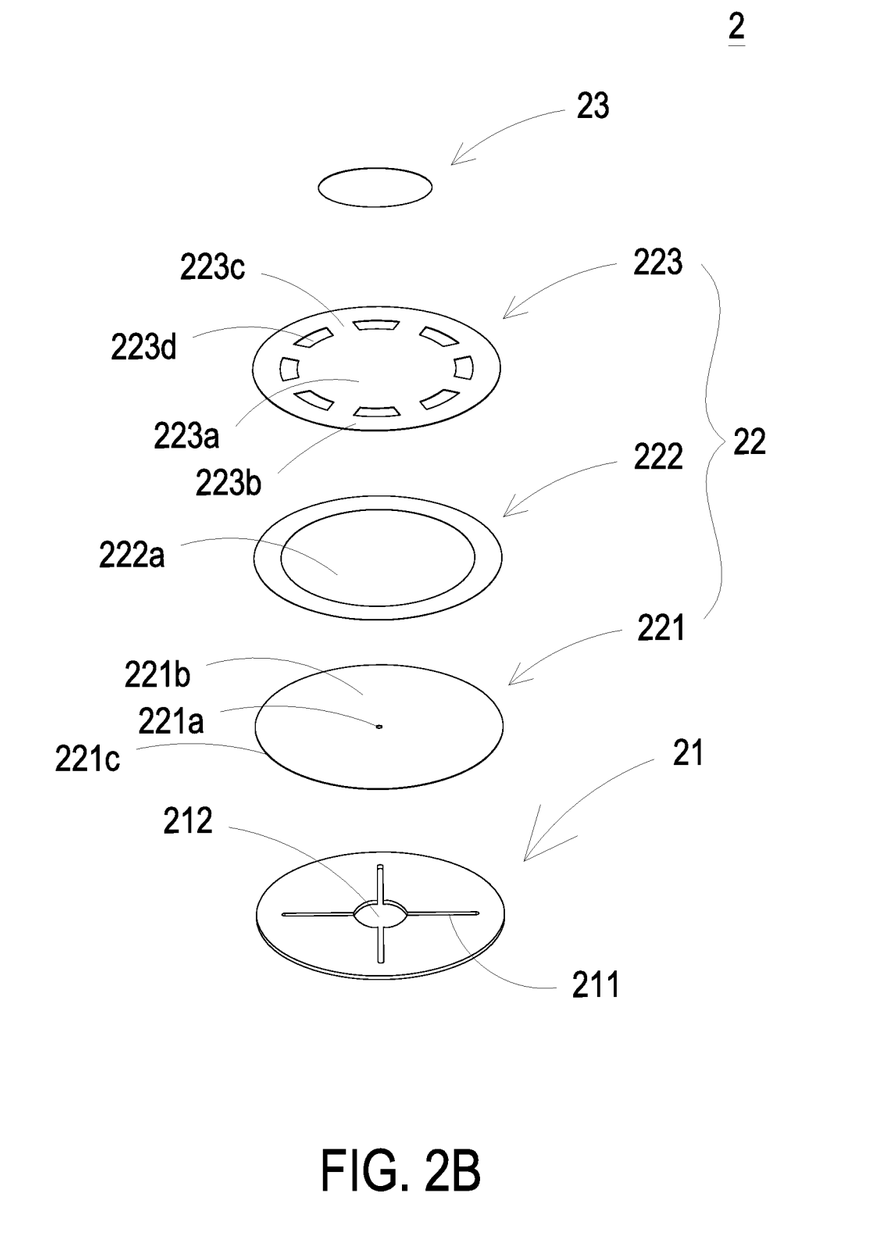
FIG. 2B is a schematic exploded view illustrating the microelectromechanical element of the blood pressure detection device according to the embodiment of the present disclosure.

Please refer to FIG. 1, FIG. 2A and FIG. 2B. In the embodiment, the microelectromechanical element 2 manufactured by a semiconductor process is stacked and integrally formed on the microelectromechanical-element region 1a of the substrate 1, and corresponds to the at least one inlet aperture 11 of the substrate 1 to actuate transportation of gas, so that the gas is inhaled through the inlet aperture 11. In the embodiment, the microelectromechanical element 2 includes an oxidation layer 21, a vibration layer 22 and a piezoelectric component 23.

In the embodiment, the oxidation layer 21 is formed and stacked on the microelectromechanical-element region 1a of the substrate 1 by a deposition process. Moreover, the oxidation layer 21 includes a plurality of convergence channels 211 and a convergence chamber 212 formed by an etching process. In the embodiment, the plurality of convergence channels 211 are in fluid communication between the convergence chamber 212 and the at least one inlet aperture 11 of the substrate 1. Preferably but not exclusively, the deposition process is one selected from the group consisting of a physical vapor deposition process (PVD), a chemical vapor deposition process (CVD) and a combination thereof. The deposition process is not redundantly described hereafter.

In the embodiment, the vibration layer 22 is formed and stacked on the oxidation layer 21 by a deposition process, and includes a metal layer 221, a second oxidation layer 222 and a silicon chip layer 223. The metal layer 221 is formed and stacked on the oxidation layer 21 by a deposition process and includes a through hole 221a, a vibration portion 221b and a fixed portion 221c formed by an etching process. Preferably but not exclusively, the etching process is one selected from the group consisting of a wet etching process, a dry etching process and a combination thereof. The etching process is not redundantly described hereafter.

In the embodiment, the through hole 221a is manufactured by the etching process and formed at a center of the metal layer 221. The vibration portion 221b is disposed around a peripheral region of the through hole 221a. The fixed portion 221c is disposed around a peripheral region of the metal layer 221.

In the embodiment, the second oxidation layer 222 is formed and stacked on the metal layer 221 by a deposition process, and includes a hollow aperture 222a formed by an etching process.

In the embodiment, the silicon chip layer 223 is formed and stacked on the second oxidation layer 222 by a deposition process and includes an actuating portion 223a, an outer peripheral portion 223b, a plurality of connecting portions 223c and a plurality of fluid channels 223d formed by an etching process. In the embodiment, the actuating portion 223a is disposed at a central part of the silicon chip layer 223. The outer peripheral portion 223b is disposed around an outer periphery of the actuating portion 223a. The plurality of connecting portions 223c are connected between the actuating portion 223a and the outer peripheral portion 223b, respectively, and each of the plurality of fluid channels 223d is disposed between the actuating portion 223a and the outer peripheral portion 223b and located between the plurality of connecting portions 223c. Furthermore, a compression chamber A is collaboratively defined by the silicon chip layer 223 and the hollow aperture 222a of the second oxidation layer 222.

In the embodiment, the piezoelectric component 23 is stacked on the actuating portion 223a of the silicon chip layer 223, and includes a lower electrode layer 231, a piezoelectric layer 232, an insulation layer 233 and an upper electrode layer 234. The lower electrode layer 231 is formed and stacked on the actuating portion 223a of the silicon chip layer 223 by a deposition process. The piezoelectric layer 232 is formed and stacked on the lower electrode layer 231 by a deposition process. The insulation layer 233 is formed and stacked on a partial surface of the piezoelectric layer 232 and a partial surface of the lower electrode layer 231 by a deposition process. The upper electrode layer 234 is formed and stacked on the insulation layer 233 and a remaining surface of the piezoelectric layer 232 without the insulation layer 233 disposed thereon by a deposition process, so as to electrically connect with piezoelectric layer 232.

Figure 3A:
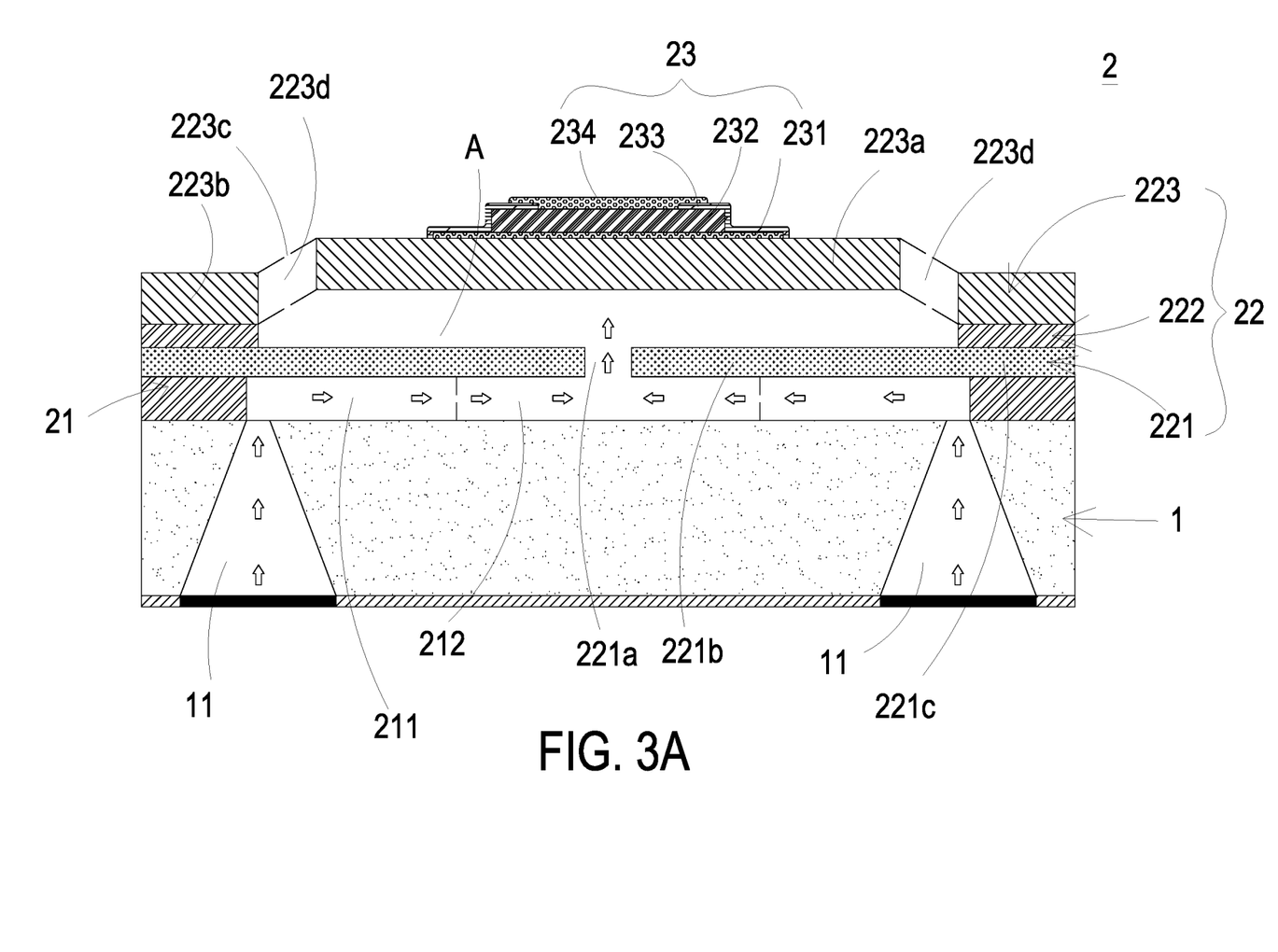
FIGS. 3A to 3C schematically illustrate the actions of the microelectromechanical element of the blood pressure detection device according to the embodiment of the present disclosure.
Figure 3B:
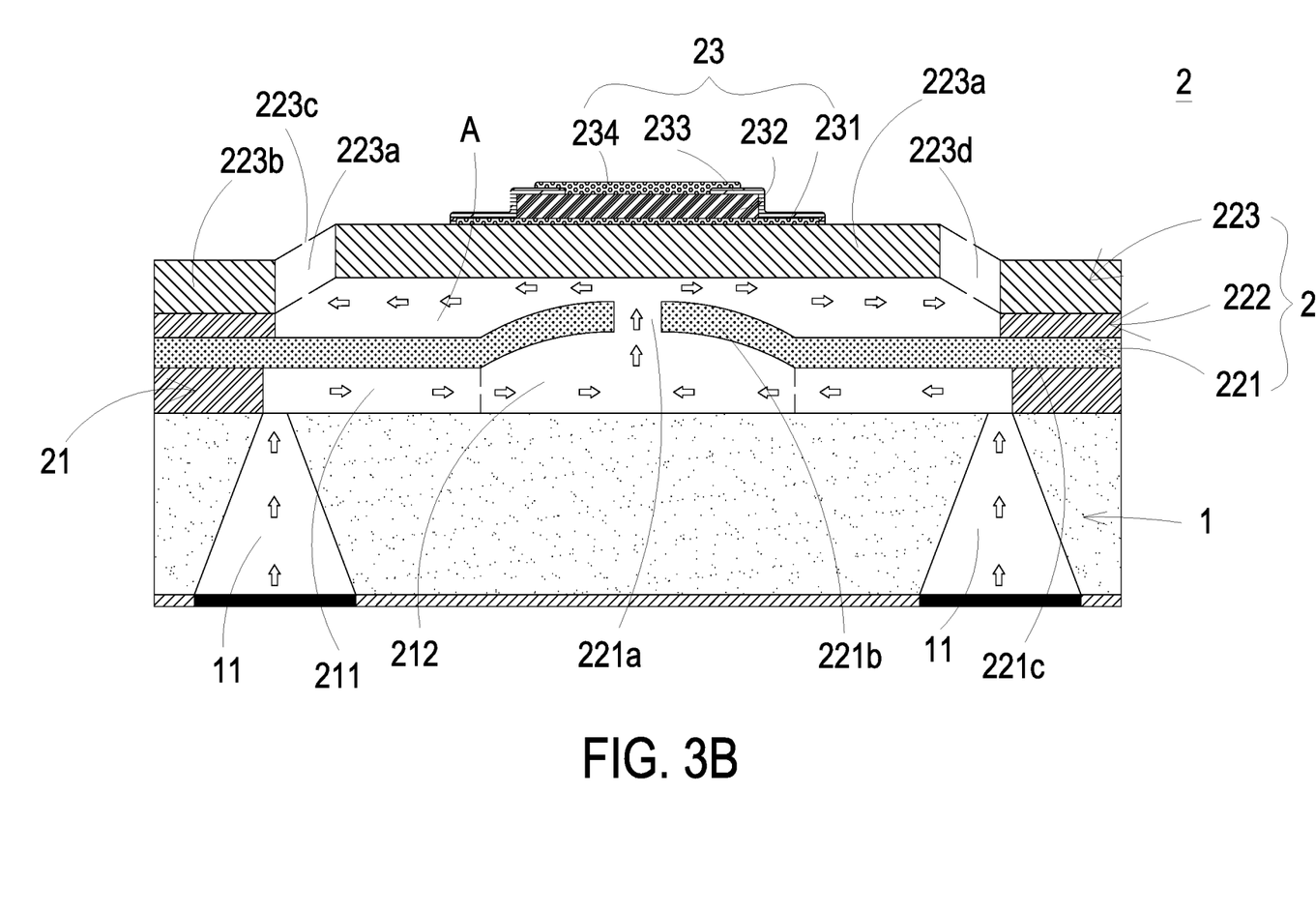
Figure 3C:
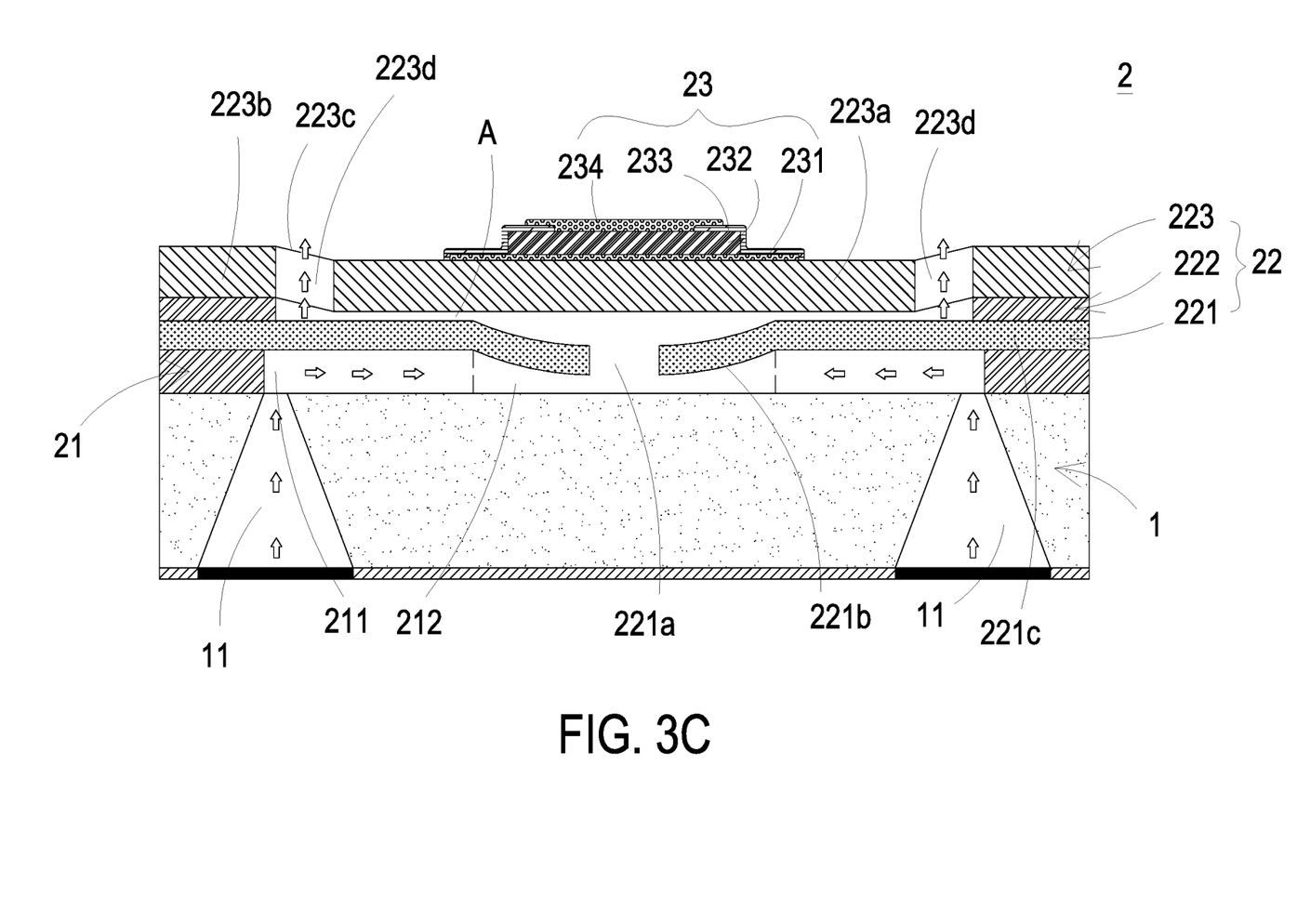

Please refer to FIGS. 3A to 3C. FIGS. 3A to 3C schematically illustrate the actions of the microelectromechanical element. As shown in FIG. 3A, when a driving signal (not shown) is received by the lower electrode layer 231 and the upper electrode layer 234 of the piezoelectric component 23, the piezoelectric layer 232 is deformed due to the influence of the reverse piezoelectric effect. In that, the piezoelectric component 23 drives the actuating portion 223a to move upwardly, the actuating portion 223a is separated away from the second oxidation layer 222 to increase the distance therebetween. At this time, the volume of the compression chamber A is expended rapidly, the internal pressure of the compression chamber A is decreased to form a negative pressure, and the gas outside the substrate 1 is inhaled through the inlet aperture 11 and further transported into the plurality of convergence channels 211 and the convergence chamber 212. Please refer to FIG. 3B. When the actuating portion 223a is driven by the piezoelectric component 23 to move upwardly, the vibration portion 221b of the metal layer 221 is moved upwardly due to the influence of the resonance principle. When the vibration portion 221b is displaced upwardly, the space of the compression chamber A is compressed and the gas in the compression chamber A is pushed to move to the fluid channels 223d of the silicon chip layer 223. Please refer to FIG. 3C. When the piezoelectric component 23 is enabled to drive the actuating portion 223a of the silicon chip layer 223 to displace downwardly, the vibration portion 221b of the metal layer 221 is driven by the actuating portion 223a to displace downwardly. In that, the gas is transported upwardly through the fluid channels 223d, and the gas in the convergence chamber 212 is compressed to flow to the compression chamber A through the through hole 221a at the same time. Thereafter, when the piezoelectric component 23 drives the actuating portion 223a to displace upwardly, the volume of the compression chamber A is greatly increased, and result in a higher suction force to inhale the gas into the compression chamber A. By repeating the actions shown in FIGS. 3A to 3C, the actuating portion 223a is continuously driven by the piezoelectric element 23 to displace upwardly and downwardly, and further to drive the vibration portion 221b to displace upwardly and downwardly. Through changing the internal pressure of the compression chamber A of the microelectromechanical element 2, the gas is inhaled and discharged continuously. Thus, the operation of the microelectromechanical element 2 for actuating transportation of the gas is achieved.

Figure 4:
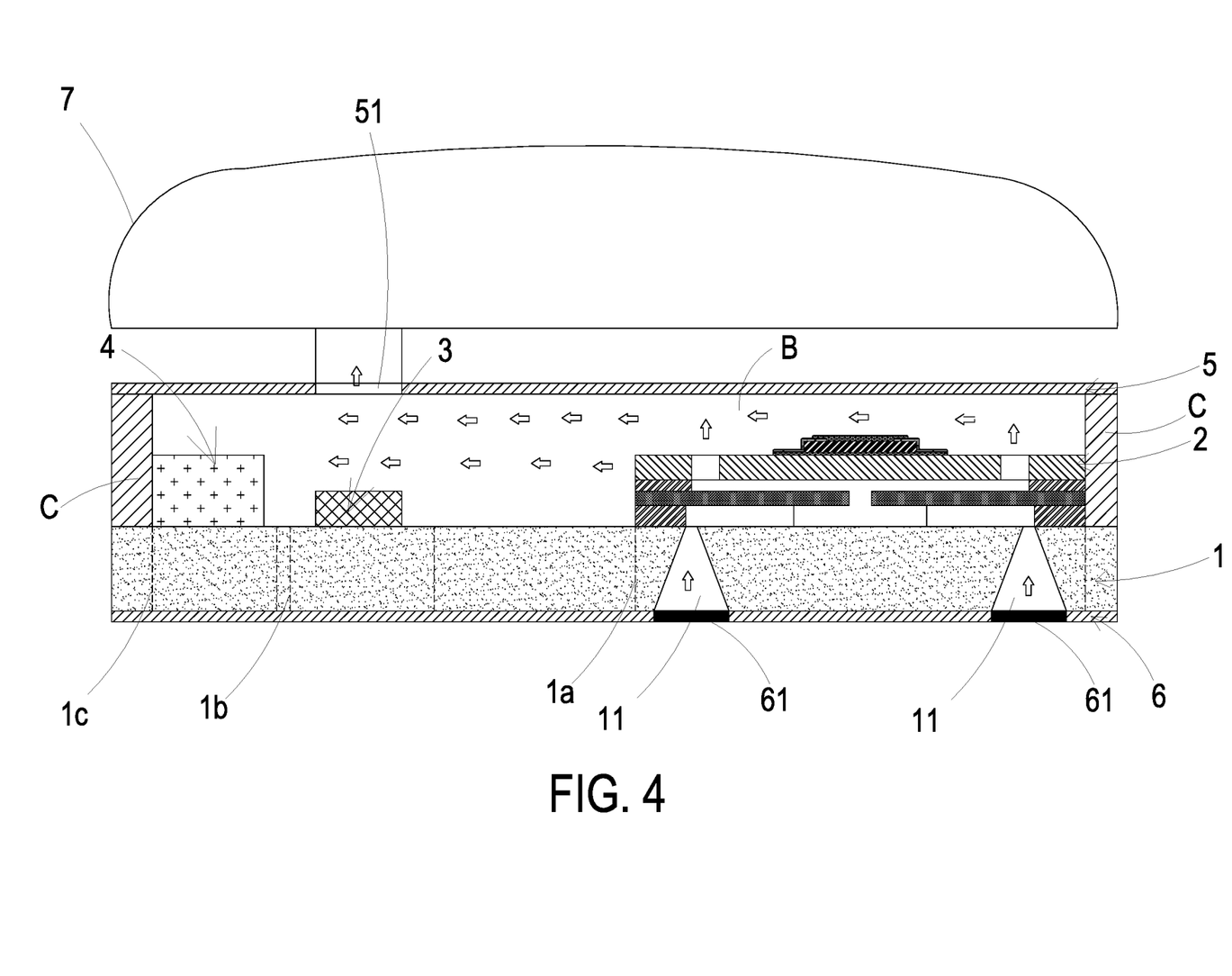
FIG. 4 schematically illustrates the action of the blood pressure detection device according to the embodiment of the present disclosure

Please refer to FIG. 1 and FIG. 4. In the embodiment, the gas-pressure-sensing element 3 manufactured by a semiconductor process is stacked and integrally formed on the gas-pressure-sensing region 1b of the substrate 1 to detect a gas pressure and generate and output a detection datum of blood pressure. In the embodiment, the driving-chip element 4 manufactured by a semiconductor process includes a microprocessor (not shown), a battery (not shown) and a communicator (not shown). The driving-chip element 4 is stacked and integrally formed on the driving-element region 1c of the substrate 1, and allows the microelectromechanical element 2 and the gas-pressure-sensing element 3 to be connected thereto. In that, the microprocessor of the driving-chip-element 4 controls driving operations of the microelectromechanical element 2 and the gas-pressure-sensing element 3, respectively. Moreover, the microprocessor of the driving-chip element 4 receives the detection datum of the blood pressure detected by the gas-pressure-sensing element 3 to calculate and output detection information about the blood pressure. The battery of the driving-chip element 4 provides a power for operations of the gas detection device. The communicator of the driving-chip element 4 receives the detection information regarding to the blood pressure outputted by the microprocessor, and the detection information is externally transmitted through the communicator of the driving-chip element 4 to an external device (not shown). Preferably but not exclusively, the communicator of the driving-chip element 4 is connected to the external device via a wireless communication transmission, so as to display the detection information received by the external device to issue a.

Please refer to FIGS. 1 and 4. In the embodiment, the encapsulation layer 5 is encapsulated and positioned on the substrate 1. In the embodiment, preferably but not exclusively, the encapsulation layer 5 is coated on the substrate 1 through a dry film C to combine with, positioned and covered above the microelectromechanical element 2, the light-emitting element 3, the particle-sensing element 4 and the gas-sensing element 5. Moreover, a flowing-channel space B is formed above the microelectromechanical element 2 and the gas-pressure-sensing element 3, and an outlet aperture 51 is formed in the encapsulation layer 5 by an etching process. In the embodiment, the outlet aperture 51 is in fluid communication with the airbag.

Figure 5A:
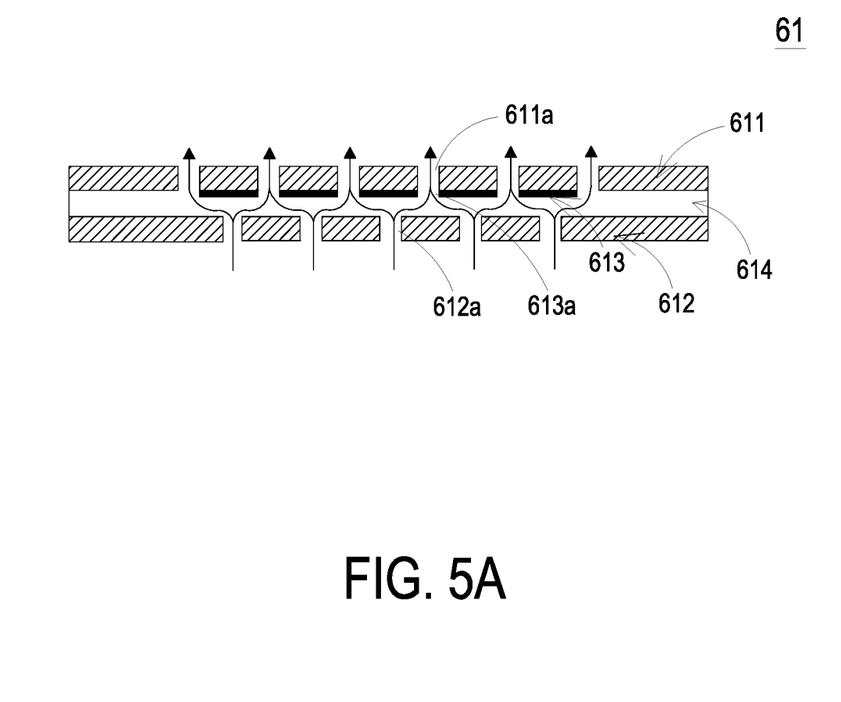
FIG. 5A is a schematic cross-sectional view illustrating valve unit of the valve layer of the blood pressure detection device opened according to the embodiment of the present disclosure.
Figure 5B:
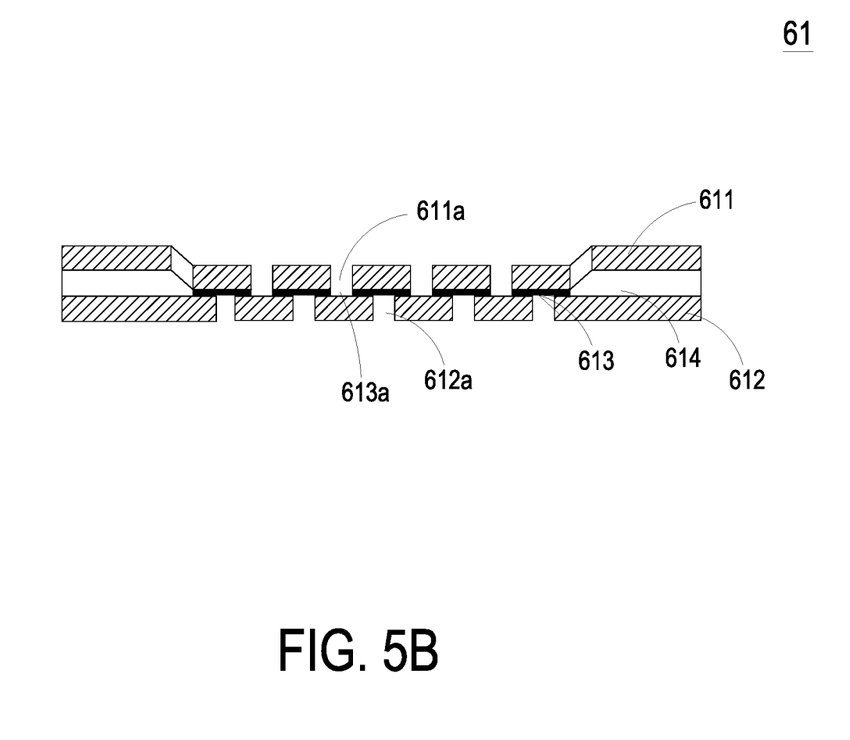
FIG. 5B is a schematic cross-sectional view illustrating valve unit of the valve layer of the blood pressure detection device closed according to the embodiment of the present disclosure.

Please refer to FIG. 1, FIG. 4, FIG. 5A and FIG. 5B. In the embodiment, the valve layer 6 is formed and stacked on a bottom of the substrate 1 by a deposition process. Moreover, a valve unit 61 is formed by an etching process at a position respectively corresponding to the inlet aperture 11 of the substrate, and the valve unit 61 is controlled by the microprocessor of the driving-chip element 4 to be opened or closed. Please refer to FIGS. 5A and 5B. In the embodiment, the valve unit 61 includes a valve conductive layer 611, a valve base layer 612 and a flexible membrane 613. In the embodiment, the valve conductive layer 611 is formed by a piezoelectric material that is electrically charged, and is electrically connected to the microprocessor to receive a driving signal from the microprocessor and deform. In the embodiment, an accommodation space 614 is maintained between the valve conductive layer 611 and the valve base layer 612. In the embodiment, the flexible membrane 613 is made of a flexible material, attached to one side of the valve conductive layer 611 and placed in the accommodation space 614. In the embodiment, a plurality of through holes 611a, 612a, 613a are formed on the valve conductive layer 611, the valve base layer 612 and the flexible membrane 613, the through hole 611a of the valve conductive layer 611 and the through hole 613a of the flexible membrane 613 are aligned to each other, and the through hole 612a of the valve base layer 612 and the through hole 611a of the valve conductive layer 611 are misaligned to each other. As shown in FIG. 5A, when the valve conductive layer 611 does not receive the driving signal from the microprocessor, the valve conductive layer 611 is maintained in the accommodation space 614 and form a distance from the valve base layer 612, so that the valve unit 61 is opened even though the through hole 612a of the valve base layer 612 and the through hole 611a of the valve conductive layer 611 are misaligned to each other. As shown in FIG. 5B, when the valve conductive layer 611 receives the driving signal, the valve conductive layer 611 is deformed and attached to the valve base layer 612, the through hole of the valve base 612 is sealed by the flexible membrane 613 since the through hole 613a of the flexible membrane 6131 and the through hole 612a of the valve base 612 are misaligned to each other, so that the valve unit 61 is closed.

As described above and shown in FIG. 4, the blood pressure detection device of the present disclosure controls the driving operations of the microelectromechanical element 2, the gas-pressure-sensing element 3 and the valve unit 61, respectively, through the microprocessor of the driving-chip element 4. When the valve unit 61 is opened and the microelectromechanical element 2 is enabled to actuate the transportation of the gas, the gas is introduced into the flowing-channel space B through the at least one inlet aperture 11 of the substrate 1, flows through the outlet aperture 51 of the encapsulation layer 5, and transported into the airbag 7 to inflate the airbag 7. The airbag is inflated and expanded to oppress the skin of a wearer. Through detecting the gas pressure state in the airbag 7 by the gas-pressure-sensing element 3, the blood pressure of the wearer can be obtained. Moreover, the detection datum of blood pressure outputted by the gas-pressure-sensing element 3 is transmitted to the microprocessor to calculate and output the detection information about the blood pressure. The detection information is externally transmitted through the communicator of the driving-chip element 4 to the external device, so that the external device is able to display the received detection information.

In summary, the present disclosure provides a blood pressure detection device having a miniaturized structure manufactured by a semiconductor process, and capable of being combined with a wearable device or a portable electronic device, which is convenient for users to carry, and capable of achieving the blood pressure measurement without being restricted by time and place.

While the disclosure has been described in terms of the most practical and preferred embodiments, it is to be understood that the disclosure needs not be limited to the disclosed embodiments. On the contrary, it is intended to cover various modifications and similar arrangements included within the spirit and scope of the appended claims so as to encompass all such modifications and similar structures.

What is claimed is:
1. A blood pressure detection device comprising:
a substrate comprising a microelectromechanical-element region, a gas-pressure-sensing region and a driving- element region, wherein at least one inlet aperture is formed in the microelectromechanical-element region by an etching process;

a microelectromechanical element manufactured by a semiconductor process is stacked and integrally formed on the microelectromechanical-element region of the substrate, and corresponds to the at least one inlet aperture to actuate transportation of gas;

a gas-pressure-sensing element manufactured by a semiconductor process is stacked and integrally formed on the gas-pressure-sensing region of the substrate, so as to detect a gas pressure and output a detection datum of blood pressure;

a driving-chip element manufactured by a semiconductor process is stacked and integrally formed on the driving-element region, wherein the driving-chip element is electrically connected to the microelectromechanical element and the gas-pressure-sensing element, and comprises a microprocessor;

an encapsulation layer positioned on the substrate and configured to encapsulate at least the microelectromechanical element and the gas-pressure-sensing element, wherein a flowing-channel space is formed above the microelectromechanical element and the gas-pressure-sensing element, an outlet aperture is manufactured in the encapsulation layer by an etching process, and the outlet aperture is in fluid communication with an airbag; and a valve layer formed and stacked on a bottom of the substrate by a deposition process, wherein a valve unit is formed in the valve layer by an etching process at a position corresponding to the at least one inlet aperture of the substrate, and the valve unit is controlled by the microprocessor of the driving-chip element to be opened or closed;

wherein the microprocessor of the driving-chip element controls driving operations of the microelectromechanical element, the gas-pressure sensing element and the valve unit, respectively, wherein when the valve unit is opened and the microelectromechanical element is enabled to actuate the transportation of the gas, the gas is introduced into the flowing-channel space through the at least one inlet aperture of the substrate, flows through the outlet aperture of the encapsulation layer, and is transported into and inflates the airbag for carrying out blood pressure measurement, and the detection datum of blood pressure outputted by the gas-pressure-sensing element is transmitted to the microprocessor.

2. The blood pressure detection device according to claim 1, wherein the microelectromechanical element comprises:

an oxidation layer formed and stacked on the microelectromechanical-element region of the substrate by a deposition process, wherein the oxidation layer comprises a plurality of convergence channels and a convergence chamber formed by an etching process, and the plurality of convergence channels are in fluid communication between the convergence chamber and the at least one inlet aperture of the substrate;

a vibration layer formed and stacked on the oxidation layer by a deposition process, and comprising:

a metal layer formed and stacked on the oxidation layer by a deposition process and comprising a through hole, a vibration portion and a fixed portion formed by an etching process, wherein the through hole is formed at a center of the metal layer, the vibration portion is disposed around a peripheral region of the through hole, and the fixed portion is disposed at a peripheral region of the metal layer;

a second oxidation layer formed and stacked on the metal layer by a deposition process, and comprising a hollow aperture formed by an etching process; and a silicon chip layer formed and stacked on the second oxidation layer by a deposition process and comprising an actuating portion, an outer peripheral portion, a plurality of connecting portions and a plurality of fluid channels formed by an etching process, wherein the actuating portion is disposed at a central part of the silicon chip layer, the outer peripheral portion is disposed around an outer periphery of the actuating portion, the plurality of connecting portions are connected between the actuating portion and the outer peripheral portion, respectively, and each of the plurality of fluid channels is disposed between the actuating portion and the outer peripheral portion and located between two of the plurality of connecting portions, wherein a compression chamber is defined by a combination of the silicon chip layer and the hollow aperture of the second oxidation layer; and a piezoelectric component formed and stacked on the actuating portion of the silicon chip layer by a deposition process, wherein the piezoelectric component comprises a lower electrode layer, a piezoelectric layer, an insulation layer and an upper electrode layer, wherein the piezoelectric layer is formed and stacked on the lower electrode layer by a deposition process, the insulation layer is formed and stacked on a partial surface of the piezoelectric layer and a partial surface of the lower electrode layer by a deposition process, and the upper electrode layer is formed and stacked on the insulation layer and a remaining surface of the piezoelectric layer without the insulation layer disposed thereon by a deposition process, so as to electrically connect with piezoelectric layer.

3. The blood pressure detection device according to claim 1, wherein the driving-chip element comprises a battery to provide a operation power for the blood pressure detection device.

4. The blood pressure detection device according to claim 1, wherein the microprocessor comprises a communicator, and the detection datum of blood pressure outputted from the microprocessor is received by the communicator and externally transmitted to an external device, so as to allow the external device to display the detection datum.

5. The blood pressure detection device according to claim 4, wherein the communicator is connected to the external device via a wireless communication transmission.

6. The blood pressure detection device according to claim 1, wherein the valve unit comprises a valve conductive layer, a valve base layer and a flexible membrane, wherein the valve conductive layer is formed by a piezoelectric material that is electrically charged, and is electrically connected to the microprocessor, whereby the valve conductive layer deforms when a driving signal from the microprocessor is received, wherein an accommodation space is maintained between the valve conductive layer and the valve base layer, and the flexible membrane is made of a flexible material, attached to one side of the valve conductive layer and placed in the accommodation space, wherein a plurality of through holes are formed on each of the valve conductive layer, the valve base layer and the flexible membrane, the through holes of the valve conductive layer and the through holes of the flexible membrane are aligned to each other, and the through holes of the valve base layer and the through holes of the valve conductive layer are misaligned to each other.

7. The blood pressure detection device according to claim 6, wherein when the valve conductive layer does not receive the driving signal from the microprocessor, the valve conductive layer is maintained in the accommodation space and is distanced from the valve base layer, so that the valve unit is opened.

8. The blood pressure detection device according to claim 6, wherein when the valve conductive layer receives the driving signal of the microprocessor, the valve conductive layer is deformed and attached to the valve base layer, so that the valve unit is closed.

* * * * *